(«19») United States Patent
Mizuno et al.

[11] Patent Number: 5,554,758
[45] Date of Patent: Sep. 10, 1996

[54] METHOD FOR PRODUCING ETHERS

[75] Inventors: Yukio Mizuno, Toyono-gun; Miichiro Arita, Nara, both of Japan

[73] Assignee: Takeda Chemical Industries, Ltd., Osaka, Japan

[21] Appl. No.: 474,133

[22] Filed: Jun. 7, 1995

Related U.S. Application Data

[63] Continuation of Ser. No. 352,184, Dec. 1, 1994, abandoned, which is a continuation of Ser. No. 121,291, Sep. 15, 1993, abandoned, which is a continuation of Ser. No. 855,798, Mar. 23, 1992, abandoned.

[30] Foreign Application Priority Data

Mar. 25, 1991 [JP] Japan ..................................... 3-060208

[51] Int. Cl.$^6$ ....................... C07D 213/28; C07D 213/30
[52] U.S. Cl. .......................... 546/250; 546/252; 546/339; 546/340
[58] Field of Search ..................................... 546/250, 252, 546/339, 340

[56] References Cited

U.S. PATENT DOCUMENTS 4,812,570  3/1984  Meguro et al. .......................... 546/280

OTHER PUBLICATIONS

CA 113:97508j, 1990.
March, Advanced Organic Chemistry, pp. 357–358, 2nd Edition, 1977.

*Primary Examiner*—Ba Kim Trinh
*Attorney, Agent, or Firm*—Wenderoth, Lind & Ponack

[57] ABSTRACT

A compound of the formula:

$$A-CH_2CH_2-O-B$$

[wherein A stands for an aromatic ring residue, a group shown by $R^1$—CO— (wherein $R^1$ stands for an aliphatic hydrocarbon residue, aromatic hydrocarbon residue, a heterocyclic residue, an aromatic alipahtic hydrocarbon residue or an alicyclic hydrocarbon residue) or $R^2$—CH=CH— (wherein $R^2$ stands for an aliphatic hydrocarbon residue an aromatic hydrocarbon residue a heterocyclic residue an aromatic aliphatic hydrocarbon residue or an alicyclic hydrocarbon residue), and B stands for an aromatic ring residue], can be obtained in high yield, at high purity level by short reaction time, by reacting a compound of the formula:

$$A-CH_2CH_2-X$$

(wherein A is of the same meaning as defined above, and X stands for a leaving group) with a compound represented by the general formula:

$$MO-B$$

(wherein M stands for an alkali metal atom or an alkaline earth metal atom and B is of the same meaning as defined above) in a non-aqueous solvent.

6 Claims, No Drawings

METHOD FOR PRODUCING ETHERS

This application is a continuation of now abandoned application Ser. No. 08/352,184, filed Dec. 1, 1994 which is a continuation of now abandoned application Ser. No. 08/121,291, filed Sep. 15, 1993, which application is a continuation of now abandoned application Ser. No. 07/855,798, filed Mar. 23, 1992.

This invention relates to an industrially advantageous method of preparing ethers useful as intermediates for synthesis of, among others, medicines.

As compounds having phenol ether linkage in the molecule, for example, thiazolidinedione derivatives having an action of lowering blood sugar and blood lipid have been known [JPA S55(1980)-22636, JPA S55(1980)-64586]. According to the references, a 2-pyridyl ethanol is employed as the starting material, which is subjected to substitution reaction with p-fluoronitrobenzene on the benzene ring to form phenol ether linkage, followed by reduction of the nitro group and Meerwein acylation, then thiazolidine ring is formed to thereby prepare the desired thiazolidinedione derivative. However, p-fluoronitrobenzene employed for the reaction of forming phenol ether linkage is relatively expensive and hardly available in a large amount, and, moreover, for forming the thiazolidinedione ring by converting the nitro group of the reaction product to carbon chain, a number of reaction steps are required, thus these methods are hardly considered to be industrially advantageous.

On the other hand, as an industrially advantageous method, there has been known a method of preparing a 2,4-thiazolidinedione derivative, which comprises subjecting a 2-pyridyl ethanol to tosylation, followed by subjecting the resultant to Williamson synthesis with p-hydroxybenzaldehyde [JPA S63(1988)-139182]. This method has, as compared with above-mentioned methods of preparing thiazolidinedione derivatives, less reaction steps, and affords the desired thiazolidinedione derivatives in a relatively high yield, but the Williamson synthesis, one of the steps of this reaction route, gives various by-products requiring troublesome steps for separating from the desired product.

The present invention is to provide an industrially advantageous method of preparing ethers which can be used as intermediates for the synthesis of, among others, medicines.

The present invention relates to a method of preparing an ether compound represented by the general formula:

A—CH$_2$CH$_2$—O—B    (III)

[wherein A stands for an aromatic ring residue, a group shown by R$^1$—CO— (wherein R$^1$ stands for an aliphatic hydrocarbon residue, aromatic hydrocarbon residue, a heterocyclic residue, an aromatic aliphatic hydrocarbon residue or an alicyclic hydrocarbon residue) or R$^2$—CH=CH— (wherein R$^2$ stands for an aliphatic hydrocarbon residue, an aromatic hydrocarbon residue, a heterocyclic residue, an aromatic aliphatic hydrocarbon residue or an alicyclic hydrocarbon residue); and B stands for an aromatic ring residue], which comprises reacting a compound represented by the general formula:

A—CH$_2$CH$_2$—X    (I)

[wherein A is of the same meaning as defined above; and X stands for a leaving group] with a compound represented by the general formula:

MO—B    (II)

[wherein M stands for an alkali metal atom or an alkaline earth metal atom; and B is of the same meaning as defined above] in a non-aqueous solvent.

In the above-mentioned general formulas (I) and (III), examples of the aromatic ring residue shown by A include an aromatic hydrocarbon residue and aromatic heterocyclic residue. Examples of the aromatic hydrocarbon residue include phenyl group and naphthyl group, and those of the aromatic heterocyclic residue include groups having 1 to 4 oxygen atoms, sulfur atoms and nitrogen atoms as atoms forming the ring, such as furyl group (2-furyl, 3-furyl), thienyl group (2-thienyl, 3-thienyl), pyridyl group (2-pyridyl, 3-pyridyl, 4-pyridyl), thiazolyl (2-thiazolyl, 4-thiazolyl, 5-thiazolyl), triazolyl (1,2,4-triazol-1-yl, 1,2,3-triazol-1-yl, 1,3,4-triazol-l-yl, 1,2,5-triazol1-yl), tetrazolyl (1-tetrazolyl, 5-tetrazolyl), etc. These groups tend to cause beta-elimination of group —O—B in the compound (III).

These aromatic ring residues may have substituents at optional positions on the ring. Those substituents may be any one, so long as they do not exert undesirable influence on the reaction. Examples of these substituents include alkyl groups having 1 to 6 carbon atoms such as methyl, ethyl, n-propyl, i-propyl, n-butyl, i-butyl, n-pentyl, i-pentyl, neopentyl or n-hexyl, preferably those having 1 to 3 carbon atoms; alkoxy groups having 1 to 4 carbon atoms such as methoxy, ethoxy, n-propoxy, i-propoxy, n-butoxy or t-butoxy, preferably those having 1 to 3 carbon atoms; a halogen atom such as fluorine, chloride, bromine, etc.; alkanoyloxy groups having not more than 6 carbon atoms, such as formyloxy, acetyloxy, propionyloxy, butyryloxy, isobutyryloxy, pivaloyloxy or hexanoyloxy; aryl carbonyloxy groups such as benzoyloxy and 1-naphthoyloxy; and alkoxycarbonyloxy groups having 2 to 5 carbon atoms such as methoxycarbonyloxy or ethoxycarbonyloxy.

In R$^1$—CO— and R$^2$—CH=CH— shown by A, aliphatic hydrocarbon residues shown by R$^1$ and R$^2$ are exemplified by alkyl groups having 1 to 6 carbon atoms such as methyl, ethyl, n-propyl, i-propyl, n-butyl, i-butyl, t-butyl, n-pentyl, i-pentyl, neopentyl or n-hexyl, preferably ones having 1 to 3 carbon atoms; and alkenyl groups having not more than 5 carbon atoms, such as vinyl and allyl.

Examples of the aromatic hydrocarbon residues shown by R$^1$ and R$^2$ include phenyl and naphthyl, and those of the aromatic aliphatic hydrocarbon residues shown by R$^1$ and R$^2$ include benzyl, phenethyl, naphthylmethyl and naphthylethyl. Examples of the heterocyclic residues include, besides the aromatic heterocyclic residues included in the aromatic ring residue shown by A, tetrahydrofuranyl, dihydrofuranyl, tetrahydro-thienyl, dihydrothienyl, tetrahydropyranyl, dihydropyranyl, piperidinyl, morpholinyl, pyrrolidinyl, piperazinyl and N-methyl piperazinyl.

These aromatic hydrocarbon residues, heterocyclic residues and aromatic aliphatic hydrocarbon residues may have substituents at optional positions on the ring. Examples of such substituents include the same substituents on the aromatic ring residue shown by A.

Examples of the alicyclic hydrocarbon residues shown by R$^1$ and R$^2$ include cycloalkyl groups having 3 to 7 carbon atoms such as cyclopropyl group, cyclobutyl group, cyclopentyl group and cyclohexyl group.

In the above-mentioned general formula (I), examples of the leaving groups shown by X include halogen (chlorine, bromine, iodine, etc.), alkyl sulfonyloxy groups (ones having 1 to 3 carbon atoms such as methylsulfonyloxy, ethylsulfonyloxy, propylsulfonyloxy, etc.), and aryl sulfonyloxy (ones having 6 to 8 carbon atoms such as phenylsulfonyloxy and p-toluenesulfonyloxy). Among them, arylsulfonyloxy groups or alkylsulfonyloxy groups are preferable.

In the above-mentioned general formula (II), the alkali metal atom shown by M is exemplified by potassium, sodium or lithium, and the alkaline earth metal atom shown by M is exemplified by magnesium calcium, strontium or barium.

In the above-mentioned general formulas (II) and (III), as the aromatic ring residue shown by B, mention is made of the same ones as those shown by A. As substituents on these residues, mention is made of, besides the substituents on aromatic ring residues shown by A, aidehyde, for example.

In the method of this invention, the reaction between the compound (I) and the compound (II) is conducted in a non-aqueous solvent. The non-aqueous solvent means an organic solvent containing substantially no water, more specifically an organic solvent whose water-content is not more than 5%, preferably 3% or less. Examples of the solvent include alcohols such as methanol, ethanol, propanol, isopropanol, butanol, isobutanol or t-butanol; ketones such as acetone, methyl ethyl ketone, diethyl ketone or methyl isobutyl ketone; ethers such as dioxane or tetrahydrofuran; aliphatic halogenated hydrocarbons such as dichloroethane or chloroform; acetonitrile, N,N-dimethylformamide, dimethyl sulfoxide, hexamethylphosphorous triamide, etc., and these solvents can be used singly or as a suitable mixture of them. Especially, use of hydrophilic solvents, i.e. alcohols, ketones, ethers, acetonitrile, N,N-dimethyl-formamide, dimethylsulfoxide and hexamethylphosphorus triamide is preferable.

The volume of the solvent to be employed is 5–30 times as much weight relative to the compound (1), preferably 10–15 times as much weight. As the said non-aqueous solvents, while those containing relatively as little water as possible are preferable, those whose water-content is 5% or less are practically usable. When the non-aqueous solvent contains relatively much water, the yield becomes poor due to the formation of hydrate of the compound (II) or dissociation. The amount of the compound (II) to be employed is in an excess amount relative to one mole of the compound (I), preferably 1.5 to 2 mol. The reaction temperature ranges from room temperature to the reflux temperature of the solvent used. However, since the compound (I) tends to cause beta-elimination reaction, preferable reaction temperatures range from 50° to 120° C., more preferably from 70° to 90° C., when taking the relation of beta-elimination reaction with the reaction time into consideration. While the reaction time varies with reaction conditions such as reaction temperature, it usually ranges from one to 15 hours when the reaction is conducted at 50° to 120° C., and usually ranges from 3 to 6 hours when the reaction is conducted at 70° to 90° C.

While the end product (III) can be isolated and purified by subjecting the reaction mixture to conventional separation and purification processes, the reaction mixture can be used as it is for the subsequent reaction step, because the content of the end product (III) in the reaction mixture is relatively high.

The compound represented by the above-mentioned general formula (I) can be produced by, for example, allowing a compound represented by the general formula, A—$CH_2CH_2$—OH (IV) [wherein A is of the same meaning as defined above], to react with a halogenating agent or sulfonyl halide.

As the halogenating agent, mention is made of, for example, thionyl chloride, phosphorus oxychloride and phosphorus tribromide, and, examples of sulfonyl halide include alkane sulfonyl halide having 1 to 4 carbon atoms such as methane sulfonyl chloride, ethane sulfonyl chloride or propane sulfonyl bromide, and arene sulfonyl halide having 6 to 8 carbon atoms such as benzene sulfonyl chloride, p-toluenesulfonyl chloride or p-toluenesulfonyl bromide. Among them, alkane- and arene-sulfonyl halides are preferable. The amount of the halogenating agent or sulfonyl halides ranges from 1 to 3 times as much mol., preferably from 1 to 1.2 times as much mol., relative to the compound This reaction is conducted usually in a solvent in the presence of a base. The solvent is exemplified by aliphatic halogenated hydrocarbon such as dichloroethane and chloroform; ethers such as tetrahydrofuran and dioxane; ketones such as acetone and methyl ethyl ketone; acetonitrile, N,N-dimethylformamide or a suitable mixture of these solvents and water. Examples of the base include tertiary amines such as triethylamine, tripropylamine tributylamine and pyridine; alkali metal hydroxides such as sodium hydroxide and potassium hydroxide; alkali metal carbonates such as sodium carbonate and potassium carbonate; and, besides, sodium hydride and sodium acetate.

The amount of the base to be employed ranges from 1 to 3 times as much mol., preferably 1 to 1.2 times as much mol. relative to the compound (IV). This reaction is conducted usually at temperatures ranging from 0 to 40° C., preferably 0° to 25° C. The reaction time usually ranges from 0.5 to 5 hours.

The reaction of this invention can be applied to synthesis of various compounds, as exemplified below. By allowing a compound of the general formula wherein A is 5-ethyl-2-pyridyl group, to react with a compound of the general formula (II), wherein B is phenyl group having formyl group at p-position, according to the method of this invention, 4-[2-(5-ethyl-2-pyridyl) ethoxy]benzaldehyde is produced. By subjecting this product and 2,4-thiazolidinedione to Knoevenagel reaction in the presence of a suitable base, 5-[4-[2-(5-ethyl-2-pyridyl)ethoxy]benzylidene]-2,4-thiazolidinedione is obtained. By subjecting this compound to reduction, 5-[4-[2-(5-ethyl-2-pyridyl)ethoxy]benzyl]-2,4-thiazolidinedione is obtained having an action of lowering blood sugar and blood lipid, which is useful as a medicine for the therapy of, among others, diabetes. Since the end product obtained by the method of this invention contains no impurities requiring troublesome steps for eliminating them, as compared with the product obtained by the method described in JPA S63(1988)-139182, its isolation and purification can be conducted by simple processes. And, even by using the reaction mixture containing 4-[2-(5-ethyl-2pyridyl)ethoxy]benzaldehyde for the subsequent condensation reaction with 2,4-thiazolidinedione, 5-[4-[2-(5-ethyl-2-pyridyl) ethoxy]benzilidene]-2,4-thiazolidinedione can be obtained in a higher yield. Further, even when the product thus obtained is used for the subsequent reduction step as it is, i.e. without purification, 5-[4-[2-(5-ethyl-2-pyridyl)-ethoxy]benzyl]-2,4-thiazolidinedione can be obtained in a high yield.

According to the method of this invention, phenol ethers of high quality can be produced with shorter reaction time and in a higher yield, as compared with known methods, bringing about good results for the yield and quality in the subsequent reaction step. And, the method of this invention can be conducted with high safety and good operability, thus being of remarkable industrial advantage.

Reference Example 1

Production of potassium 4-formylphenolate

In 1.08 liter of ethanol was dissolved 81.3 g of potassium hydroxide (content 85%) under stirring. In the solution was dissolved 150 g of p-hydroxybenzaldehyde at room temperature, which was stirred further for one hour. The reaction mixture was concentrated under reduced pressure. To the concentrate was added 350 ml of ethanol, which was concentrated again. To the solid concentrate was added 200 ml of ethanol, to which was further added 2.1 liters of diisopropyl ether, then the mixture was stirred for one hour at room temperature. Resulting precipitates were collected by filtration under reduced pressure and washed with 150 ml of diisopropyl ether, followed by drying at 40° C. under reduced pressure to give 197 g (yield 100%) of potassium 4-formylphenolate.

Reference Example 2

Production of (5-ethyl-2-pyridyl)ethyl methanesulfonate

In 800 ml of methylene chloride was dissolved 80 g of (5-ethyl-2-pyridyl)ethanol, to which was added 55 g of triethylamine. To this mixture was added dropwise gradually 73.2 g of methanesulfonyl chloride while stirring under cooling, and the mixture was stirred for 3 hours at room temperature. To the reaction mixture was added 400 ml of water. The aqueous layer was separated and subjected to re-extraction, which was combined with the extracted organic layer. The resultant organic layer was washed with 400 ml of a saturated aqueous solution of sodium hydrogencarbonate, then with a saturated aqueous saline solution, followed by drying over anhydrous sodium sulfate. The solvent was distilled off under reduced pressure to give 121 g (100 %) of (5-ethyl-2-pyridyl)ethyl methanesulfonate as a pale yellow oily product.

IR(Neat) ν $cm^{-1}$: 1360, 1200, 1180

NMR(CDCl$_3$) δppm: 1.23 (3H,t,J=7.5Hz), 2.65(2H,q,J=7.5Hz), 2.88(3H,s), 3.20(2H,t,J=6.5Hz), 4.62(2H,t,J=6.5Hz), 7.17(1H,d,J=7.5Hz), 7.52(1H,dd,J=7.5Hz, 3.0Hz), 8.38(1H,d,J=3.0Hz)

Reference Example 3

Production of (5-ethyl-2-pyridyl)ethyl p-toluenesulfonate 7.1 g of sodium hydroxide was dissolved in 33 ml of water, and 7.6 g of (5-ethyl-2-pyridyl)ethanol was dissolved in 33 ml of tetrahydrofuran. Both solutions were mixed and cooled. To the resultant solution was added dropwise gradually at 0° C. a solution of 11.7 g of p-toluenesulfonyl chloride in 51 ml of tetrahydrofuran, followed by stirring for 2 hours at the same temperature. To the reaction mixture was added ice water. The mixture was extracted twice with 100 ml each of methylene chloride. The extracted organic layers are combined. The resultant organic layer was washed with water and dried over anhydrous sodium sulfate. The solvent was distilled off under reduced pressure, whereby 14.4 g of (5-ethyl-2-pyridyl)ethane p-toluenesulfonate was obtained as a pale yellow oily product.

IR(Neat) ν $cm^{-1}$: 1360, 1190, 1180

NMR(CDCl$_3$) δppm: 1.22(3H,t,J=7.5Hz), 2.41(3H,s), 2.60(2H,q,J=7.5Hz), 3.08(2H,t,J=6.8Hz), 4.41(2H,t,J=6.8Hz), 7.03(1H,d,J=7.6Hz), 7.26(2H,d,J=7.5Hz), 7.41(1H,dd,J=7.6Hz, 3.0Hz), 7.68(2H,d,J=7.5Hz), 8.25(1H,d,J=3.0Hz)

Example 1 a) Production of 4-[2-(5-ethyl-2-pyridyl)ethoxy]benzaldehyde

In 850 ml of ethanol were dissolved 72 g of (5-ethyl-2-pyridyl) ethyl-2-pyridyl)ethyl methanesulfonate and 85.5 g of potassium 4-formylphenolate, then the solution was stirred for 6.5 hours under reflux. The reaction mixture was concentrated under reduced pressure. To the concentrate was added 850 ml of ethyl acetate, which was washed with 700 ml each portion of a 0.2N aqueous solution of caustic soda five times and with 700 ml each portion of water twice, followed by drying over anhydrous sodium sulfate. The organic layer was processed with 7.0 g of activated charcoal, then the solvent was distilled off under reduced pressure to leave 67 g of an oily product containing 4-[2-(5-ethyl-2-pyridyl) ethoxy]benzaldehyde. This product was purified by means of a silica gel column chromatography to give 56.0 g of 4-[2-(5-ethyl-2-pyridyl)ethoxy]benzaldehyde as a pale yellow oily product. [The yield based on (5-ethyl-2-pyridyl)ethyl methanesulfonate was 70.0%.]. This product was in complete agreement with the authentic sample in IR(Neat) and NMR(CDCl3) data.

IR(Neat) ν $cm^{-1}$: 1695, 1605, 1580, 1260, 1160

10 NMR(CDCl $_3$) δppm: 1.23(3H,d,J=7.5Hz), 2.63(2H,q,J=7.5Hz), 3.25(2H,t,J=6.5Hz), 4.44(2H,t,J=6.5Hz), 6.98(2H,d,J=8.5Hz), 7.17(1H,d,J=7.5Hz), 7.46(1H,dd,J=7.5Hz, 3.0Hz), 7.78(2H,d,J=8.5Hz), 8.39(1H,d,J=3.0Hz), 9.83(1H,s)

b) Production of 4-[2-! 5-ethyl-2-pyridyl)ethoxy]benzaldehyde

In 1.5 liter of ethanol were dissolved 151 g of (5-ethyl-2-pyridyl)ethyl methanesulfonate (content 94%) and 179 g of potassium 4-formylphenolate, and the solution was stirred for 5 hours under reflux. The reaction mixture was concentrated under reduced pressure. To the concentrate was added 1.7 liter of ethyl acetate, which was washed with 500 ml each portion of a 0.2N aqueous solution of caustic soda three times, then with 500 ml of water, followed by drying over anhydrous sodium sulfate. The organic layer was processed with 6.3 g of activated charcoal. The solvent was distilled off under reduced pressure to leave 141.5 g of an oily product containing 4-[2-(5-ethyl-2-pyridyl) ethoxy]benzaldehyde. This product was subjected to quantitative determination by means of HPLC to confirm that the product contained 119 g of 4-[2-(5-ethyl-2-pyridyl) ethoxy]benzaldehyde. [The yield based on (5-ethyl-2-pyridyl)ethyl methanesulfonate was 75.3%.]

c) Production of 4-[2-(5-ethyl-2-pyridyl)ethoxy]benzaldehyde

In 200 ml of ethanol were dissolved 14 g of (5-ethyl-2-pyridyl) ethyl p-toluenesulfonate and 14.7 g of potassium 4-formyl phenolate. The solution was stirred for 5 hours under reflux. The reaction mixture was concentrated under reduced pressure. To the concentrate was added 200 ml of ethyl acetate, which was washed with 100 ml each portion of a 0.2N aqueous solution of caustic soda five times, then with 150 ml 10 each portion of water twice, followed by drying over anhydrous sodium sulfate. The organic layer was processed with 1 g of activated charcoal. The solvent was distilled off under reduced pressure to leave 10.5 g of a reddish oily product containing 4-[2-(5-ethyl-2-pyridyl)ethoxy]benzaldehyde. This product was subjected to quantitative determination by means of HPLC to confirm that the product contained 8.2 g of 4-[2-(5-ethyl-2-pyridyl)ethoxy]benzaldehyde. [The yield based on (5-ethyl-2-pyridyl)ethyl methanesulfonate was 70.1%.]

Reference Example 4

Production of 5-[4-[2-(5-ethyl-2-pyridyl)ethoxy]benzilidene]-2,4-thiazolinedione In 1.1 liter of ethanol was dissolved 94 g of 4-[2(5-ethyl-2-pyridyl) ethoxy]benzaldehyde (content 80.6%) obtained by substantially the same manner as b) of Example 1. To the solution were added 93.7 g of 2,4-thiazolidinedione and 19.7 g of piperidine, and the mixture was stirred for 5 hours under reflux. The reaction mixture was gradually cooled to room temperature. Resulting crystals were collected by filtration under reduced pressure, washed with 100 ml of ethanol and dried at 50° C. under reduced pressure to give 77.1 g of 5-[4-[2-(5-ethyl-2-pyridyl)ethoxy]benzilidene]-2,4-thiazolidinedione as pale yellow crystals (content 99.5%). [The yield based on 4-[2-(5-ethyl-2-pyridyl) ethoxy]benzaldehyde was 73.0%.] This product was in complete agreement with the authentic sample, 5-[4-[2-(5-ethyl-2-pyridyl)ethoxy]benzylidene]-2,4-thiazolidinedione, in various spectrum data.

Reference Example 5

Production of 5-[4-[2-(5-ethyl-2-pyridyl)ethoxy]benzyl]-2,4-thiazolidinedione

In 600 ml of dioxane was suspended 30 g of 5-[4-[2-(5-ethyl-2-pyridyl) ethoxy]benzylidene]-2,4-thiazolidinedione obtained by substantially the same procedure as in Reference Example 4. To the suspension was added 20 g of 5% palladium-carbon (50% wet), which was subjected to catalytic reduction at 110° C. under elevated hydrogen pressure (100 kg/cm$^2$) for 2 hours. The catalyst was filtered off when hot, and the filtrate was concentrated under reduced pressure to a volume of 540 ml. Precipitating crystals were collected by filtration and dissolved in 600 ml of dioxane when hot. The solution was cooled to room temperature slowly to cause recrystallization. The crystals were collected by filtration under reduced pressure and dried at 60° C. under reduced pressure to give 21.7 g of 5-[4-[2-(5-ethyl-2-pyridyl) ethoxy]benzyl]-2,4-thiazolidinedione. [The yield was 72% based on 5-[4-[2-(5-ethyl-2-pyridyl)ethoxy]benzylidene]-2,4-thiazolidinedione.] This product was in complete agreement with the authentic sample, 5-[4-[2-(5-ethyl-2-pyridyl)ethoxy]benzyl]-2,4-thiazolidinedione,-in various spectrum data.

We claim:

1. A method of preparing an ether compound of the formula:

A—CH$_2$CH$_2$—O—B wherein A represents 5-ethyl-2-pyridyl and B represents 4-formylphenyl, which comprises reacting a compound of the formula:

A—CH$_2$CH$_2$—X wherein A is as defined above and X represnts methylsulfonyloxy or p-toluene sulfonyloxy with a compound of the formula:

MO—B wherein M represents potassium and B is as defined above in a non-aqueous solvent.

2. A method as claimed in claim 1, wherein the non-aqueous solvent is a hydrophilic solvent.

3. A method as claimed in claim 1, wherein the solvent is used in an amount of 5 to 30 weight times as much weight relative to the compound of formula: A—CH$_2$CH$_2$—X.

4. A method as claimed in claim 1, wherein the compound (MO—B) is employed in an excess amount relative to one mole of the compound of formula: A—CH$_2$CH$_2$—X.

5. A method as claimed in claim 1, wherein the reaction is carried out at a temperature ranging from 50° to 120° C.

6. A method as claimed in claim 1, wherein the reaction is carried out at a temperature ranging from 70° to 90° C.

* * * * *

UNITED STATES PATENT AND TRADEMARK OFFICE
CERTIFICATE OF CORRECTION

PATENT NO. : 5,554,758

DATED : September 10, 1996

INVENTOR(S) : YUKIO MIZUNO and MIICHIRO ARITA

Page 1 of 2

It is certified that error appears in the above-indentified patent and that said Letters Patent is hereby corrected as shown below:

Column 2, line 15, change "1,2,5-triazoll-yl" to read —1,2,5-triazol-1-yl—.

Column 3, line 4, after "magnesium" insert a comma (,);
line 10, correct the spelling of "aldehyde";
line 27, change "dimethyl-formamide" to read —dimethylformamide—.

Column 4, line 8, after "compound" insert —(IV)—;
line 16, after "tripropylamine" insert a comma (,);
line 24, change "0" to read —0°—;
line 29, after "formula" insert —(I)—.

Column 5, line 32, change "v" to read —$\nu$—;
line 54, change "v" to read —$\nu$—;
line 66, delete "2-pyridyl)ethyl".

UNITED STATES PATENT AND TRADEMARK OFFICE
CERTIFICATE OF CORRECTION

PATENT NO. : 5,554,758
DATED : September 10, 1996
INVENTOR(S) : YUKIO MIZUNO and MIICHIRO ARITA It is certified that error appears in the above-indentified patent and that said Letters Patent is hereby corrected as shown below:

Column 6, line 16, change "CDC13" to read --$CDCl_3$--;

line 17, change "v" to read -- $\nu$ --;

line 18, change "10NMR" to read --NMR--;

line 23, delete "!" and insert therefor --(--;

line 51, delete "10";

line 60, change "methanesulfonate" to read --p-toluene-sulfonate--.

Column 8, line 2, change ",-in" to read --, in--.

Signed and Sealed this

Fourth Day of March, 1997

Attest:

BRUCE LEHMAN

Attesting Officer    Commissioner of Patents and Trademarks